United States Patent
Han et al.

(10) Patent No.: US 10,912,310 B2
(45) Date of Patent: Feb. 9, 2021

(54) ELAEAGNUS ANGUSTIFOLIA YOGHOURT AND MANUFACTURING METHOD THEREOF

(71) Applicant: Qinghai Jinqilian Dairy LLC, Haibei Tibetan Autonomous Prefecture (CN)

(72) Inventors: Denglun Han, Haibei Tibetan Autonomous Prefecture (CN); Xueqin Mao, Haibei Tibetan Autonomous Prefecture (CN); Xikui Zhu, Haibei Tibetan Autonomous Prefecture (CN); Zhongyuan Zhang, Haibei Tibetan Autonomous Prefecture (CN)

(73) Assignee: Qinghai Jinqilian Dairy LLC, Haibei Tibetan Autonomous Prefecture (CN)

( * ) Notice: Subject to any disclaimer, the term of this patent is extended or adjusted under 35 U.S.C. 154(b) by 330 days.

(21) Appl. No.: 15/708,140

(22) Filed: Sep. 19, 2017

(65) Prior Publication Data

US 2018/0153183 A1 Jun. 7, 2018

(30) Foreign Application Priority Data

Dec. 7, 2016 (CN) .......................... 2016 1 1116693

(51) Int. Cl.
*A61K 36/185* (2006.01)
*A23C 9/133* (2006.01)
*A23C 9/13* (2006.01)
*A61K 36/73* (2006.01)

(52) U.S. Cl.
CPC ............ *A23C 9/133* (2013.01); *A23C 9/1307* (2013.01); *A61K 36/185* (2013.01); *A61K 36/73* (2013.01)

(58) Field of Classification Search
CPC .................................................. A61K 36/185
See application file for complete search history.

(56) References Cited

PUBLICATIONS

Sahan et al., "Bioaccessibilities of K, P, Fe and B minerals in oleaster flour as a novel food ingredients," meeting abstract, FASEB J 27(S1), 2013.*

* cited by examiner

*Primary Examiner* — Rosanne Kosson
(74) *Attorney, Agent, or Firm* — Wayne & Ken, LLC; Tony Hom

(57) ABSTRACT

The present invention discloses an *Elaeagnus angustifolia* yoghourt and a manufacturing method thereof. The yoghourt is manufactured by taking fresh milk, white granulated sugar, *Elaeagnus angustifolia*, apple pear juice and *Elaeagnus angustifolia* honey drink as main ingredients. The *Elaeagnus angustifolia* yoghourt is not only delicate in product taste and unique in flavor but also rich in nutrition and has effects of nourishing yang and moistening dryness and invigorating spleen and strengthening stomach.

2 Claims, No Drawings

ELAEAGNUS ANGUSTIFOLIA YOGHOURT AND MANUFACTURING METHOD THEREOF

FIELD OF THE INVENTION

The present invention relates to a yoghourt product, and more specifically, to an *Elaeagnus angustifolia* yoghourt and a manufacturing method thereof.

BACKGROUND OF THE INVENTION

Yoghourt is a common dairy product. At present, yoghourt is very single in taste in existing market, consumers have little choices, and it influences experience of the consumers. In addition, existing yoghourt products are very weak in functions and cannot meet needs of modern consumers for health care.

SUMMARY OF THE INVENTION

With respect to defects in the prior art, the present invention aims at providing an *Elaeagnus angustifolia* yoghourt and a manufacturing method thereof. *Elaeagnus angustifolia* is combined with apple pears and *Elaeagnus angustifolia* honey drink to serve as raw materials of the yoghourt. The yoghourt is excellent in taste and good in eating experience, and has effects of nourishing yang and moistening dryness and invigorating spleen and strengthening stomach as well as wide market prospects.

In order to achieve above purposes, a technical solution is adopted in the present invention as follows:

An *Elaeagnus angustifolia* yoghourt comprises the following raw materials in percentage by weight:

| | |
|---|---|
| fresh milk | 86%-90%; |
| yoghurt starter | 2%-4%; |
| white sugar | 2%-6%; |
| elaeagnus angustifolia powder | 1%-3%; |
| apple pear juice | 1%-2%; and |
| elaeagnus angustifolia honey drink | 1%-2%. |

A manufacturing method of the *Elaeagnus angustifolia* yoghourt comprises the following steps:

S1. selecting clean and pest-free *Elaeagnus angustifolia* for steaming, baking and milling to obtain a *Elaeagnus angustifolia* powder for later use, cleaning apple pears and juicing, and filtering the juice by using a filter cloth with granularity more than 200 meshes to obtain a apple pear juice for later use;

preparing a *Elaeagnus angustifolia* honey drink: selecting a certain amount of clean *Elaeagnus angustifolia*, adding the *Elaeagnus angustifolia* and water into a pot for boiling for 30 minutes, then adding honey, wherein a weight ratio of the added *Elaeagnus angustifolia* to the water to the honey is 2:5:3, taking a product out of the pot, and cooling to obtain an *Elaeagnus angustifolia* honey drink for later use;

S2. uniformly mixing the fresh milk, the white sugar as well as the *Elaeagnus angustifolia* powder, the apple pear juice and the *Elaeagnus angustifolia* honey drink obtained in the step S1 according to the above weight percentage, maintaining a temperature at 60° C.-70° C. for 60 minutes, and uniformly stirring for 30 minutes to obtain a mixture;

S3. homogenizing the mixture obtained in the step S2 through a homogenizer, and then enabling the mixture to enter a sterilization machine for sterilizing at 96.6° C.;

S4. then cooling to 40° C.-44° C., adding a yoghurt starter, uniformly stirring, adding sterilized wild Chinese wolfberry grains, filling, and fermenting at 40° C.-43° C. for 4-8 hours after filling completion; and S5. rapidly cooling to 4° C.-15° C. after fermenting, and performing after ripening.

The present invention has beneficial effects as follows:

Every 100 g of an edible part of *Elaeagnus angustifolia* contains 4.5 g proteins, 4.2 g fat, 74.8 g carbohydrates, 46 mg calcium, 67 mg phosphorus, 3.3 mg iron, 0.07 mg vitamin B2, 1.7 mg nicotinic acid and 7 mg vitamin C. It can be seen that the *Elaeagnus angustifolia* has high nutritive value.

In addition, the apple pears have health care effects of drying damp and strengthening spleen, softening blood vessels, harmonizing stomach, arresting vomiting and checking diarrhea, stopping coughing and removing phlegm and the like, and the *Elaeagnus angustifolia* honey drink prepared from the *Elaeagnus angustifolia* has effects of nourishing yang and moistening dryness and invigorating spleen and strengthening stomach.

The *Elaeagnus angustifolia*, the apple pear juice and the *Elaeagnus angustifolia* honey drink are used as the raw materials of the yoghourt, so that the yoghourt can achieve the effects of nourishing yang and moistening dryness and invigorating spleen and strengthening stomach and is enriched in nutrition.

In flavor, the *Elaeagnus angustifolia*, the apple pear juice and the *Elaeagnus angustifolia* honey drink have a sweet or sweet and sour flavor and also have unique taste and aroma. After added to serve as the raw materials of the yoghourt, the *Elaeagnus angustifolia*, the apple pear juice and the *Elaeagnus angustifolia* honey drink can be used as a source of the sweet flavor or the sweet and sour flavor and introduce a unique flavor to the yoghourt, thereby enriching choices of consumers and bringing a brand new eating experience for the consumers.

DETAILED DESCRIPTION OF THE INVENTION

The present invention is further described below. It should be noted that detailed embodiments and specific operation processes are given in the present embodiment on premise of the present technical solution. However, a protection scope of the present invention is not limited to the present embodiment.

An *Elaeagnus angustifolia* yoghourt comprises the following raw materials in percentage by weight:

| | |
|---|---|
| fresh milk | 86%-90%; |
| yoghurt starter | 2%-4%; |
| white sugar | 2%-6%; |
| elaeagnus angustifolia powder | 1%-3%; |
| apple pear juice | 1%-2%; and |
| elaeagnus angustifolia honey drink | 1%-2%. |

A manufacturing method of the *Elaeagnus angustifolia* yoghourt comprises the following steps:

S1. selecting clean and pest-free *Elaeagnus angustifolia* for steaming, baking and milling for later use, cleaning apple pears and juicing, and filtering the juice by using a filter cloth with granularity more than 200 meshes to obtain the apple pear juice for later use;

preparing the *Elaeagnus angustifolia* honey drink: selecting a certain amount of clean and pest-free *Elaeagnus*

*angustifolia*, adding the *Elaeagnus angustifolia* and water into a pot and boiling for 30 minutes, then adding honey, wherein a weight ratio of the added *Elaeagnus angustifolia* to the water to the honey is 2:5:3, taking a product out of the pot, and cooling to obtain an *Elaeagnus angustifolia* honey drink for later use;

S2. uniformly mixing the fresh milk, the white sugar as well as the *Elaeagnus angustifolia* powder, the apple pear juice and the *Elaeagnus angustifolia* honey drink obtained in the step S1 according to the above weight percentage, maintaining a temperature at 60° C.-70° C. for 60 minutes, and uniformly stirring for 30 minutes;

S3. homogenizing the mixture obtained in the step S2 through a homogenizer, and then enabling the mixture to enter a sterilization machine for sterilizing at 96.6° C.;

S4. then cooling to 40° C.-44° C., adding a yoghurt starter, uniformly stirring, adding sterilized wild Chinese wolfberry grains, filling, and fermenting at 40° C.-43° C. for 4-8 hours after filling completion; and S5. rapidly cooling to 4° C.-15° C. after fermenting, and performing after ripening.

Embodiment 1

An *Elaeagnus angustifolia* yoghourt comprises the following raw materials in percentage by weight:

| | |
|---|---|
| fresh milk | 86%; |
| yoghurt starter | 4%; |
| white sugar | 3%; |
| *elaeagnus angustifolia* powder | 3%; |
| apple pear juice | 2%; and |
| *elaeagnus angustifolia* honey drink | 2%. |

A manufacturing method of the *Elaeagnus angustifolia* yoghourt comprises the following steps:

S1. selecting clean and pest-free *Elaeagnus angustifolia* for steaming, baking and milling to obtain the *Elaeagnus angustifolia* powder for later use, cleaning apple pears and juicing, and filtering the juice by using a filter cloth with granularity of 200 meshes to obtain an apple pear juice for later use;

preparing the *Elaeagnus angustifolia* honey drink: selecting a certain amount of clean and pest-free *Elaeagnus angustifolia*, adding the *Elaeagnus angustifolia* and water into a pot for boiling for 30 minutes, then adding honey, taking a product out of the pot, and cooling to obtain the *Elaeagnus angustifolia* honey drink for later use, wherein a weight ratio of the added *Elaeagnus angustifolia* to the water to the honey is 2:5:3, 20 g *Elaeagnus angustifolia*, 50 g water and 30 g honey are adopted in the present embodiment, and peel scales of the *Elaeagnus angustifolia* are rubbed with water in the present step;

S2. uniformly mixing the fresh milk, the white sugar as well as the *Elaeagnus angustifolia* powder, the apple pear juice and the *Elaeagnus angustifolia* honey drink obtained in the step S1 according to a ratio, maintaining a temperature at 60° C.-70° C. for 60 minutes, and uniformly stirring for 30 minutes;

S3. homogenizing the mixture obtained in the step S2 through a homogenizer, and then enabling the mixture to enter a sterilization machine for sterilizing at 96.6° C.;

S4. cooling to 40° C.-44° C., then adding a yoghurt starter, uniformly stirring, adding sterilized wild Chinese wolfberry grains, filling, and fermenting at 40° C.-43° C. for 4-8 hours after filling completion; and S5. rapidly cooling to 4° C.-15° C. after fermenting, and performing after ripening.

Embodiment 2

An *Elaeagnus angustifolia* yoghourt comprises the following raw materials in percentage by weight:

| | |
|---|---|
| fresh milk | 90%; |
| yoghurt starter | 2%; |
| white sugar | 2%; |
| *elaeagnus angustifolia* powder | 2%; |
| apple pear juice | 2%; and |
| *elaeagnus angustifolia* honey drink | 2%. |

A manufacturing method of the *Elaeagnus angustifolia* yoghourt comprises the following steps:

S1. selecting clean and pest-free *Elaeagnus angustifolia* for steaming, baking and milling to obtain the *Elaeagnus angustifolia* powder for later use, cleaning apple pears and juicing, and filtering the juice by using a filter cloth with granularity of 200 meshes to obtain an apple pear juice for later use;

preparing the *Elaeagnus angustifolia* honey drink: selecting a certain amount of clean and pest-free *Elaeagnus angustifolia*, adding the *Elaeagnus angustifolia* and water into a pot for boiling for 30 minutes, then adding honey, taking a product out of the pot, and cooling to obtain the *Elaeagnus angustifolia* honey drink for later use, wherein a weight ratio of the *Elaeagnus angustifolia* to the water to the honey is 2:5:3, 20 g *Elaeagnus angustifolia,* 50 g water and 30 g honey are adopted in the present embodiment, and peel scales of the *Elaeagnus angustifolia* are rubbed with water in the present step;

S2. uniformly mixing the fresh milk, the white sugar as well as the *Elaeagnus angustifolia* powder, the apple pear juice and the *Elaeagnus angustifolia* honey drink obtained in the step S1 according to a ratio, maintaining a temperature at 60° C.-70° C. for 60 minutes, and uniformly stirring for 30 minutes;

S3. homogenizing the mixture obtained in the step S2 through a homogenizer, and then enabling the mixture to enter a sterilization machine for sterilizing at 96.6° C.;

S4. cooling to 40° C.-44° C., adding a yoghurt starter, uniformly stirring, adding sterilized wild Chinese wolfberry grains, filling, and fermenting at 40° C.-43° C. for 4-8 hours after filling completion; and S5. rapidly cooling to 4° C.-15° C. after fermenting, and performing after ripening.

Embodiment 3

An *Elaeagnus angustifolia* yoghourt comprises the following raw materials in percentage by weight:

| | |
|---|---|
| fresh milk | 88%; |
| yoghurt starter | 3%; |
| white sugar | 6%; |
| *elaeagnus angustifolia* powder | 1%; |
| apple pear juice | 1%; and |
| *elaeagnus angustifolia* honey drink | 1%. |

A manufacturing method of the *Elaeagnus angustifolia* yoghourt comprises the following steps:

S1. selecting clean and pest-free *Elaeagnus angustifolia* for steaming, baking and milling to obtain the *Elaeagnus*

*angustifolia* powder for later use, cleaning apple pears and juicing, and filtering the juice by using a filter cloth with granularity of 200 meshes to obtain an apple pear juice for later use;

preparing the *Elaeagnus angustifolia* honey drink: selecting a certain amount of clean and pest-free *Elaeagnus angustifolia*, adding the *Elaeagnus angustifolia* and water into a pot for boiling for 30 minutes, then adding honey, taking a product out of the pot, and cooling to obtain the *Elaeagnus angustifolia* honey drink for later use, wherein a weight ratio of the *Elaeagnus angustifolia* to the water to the honey is 2:5:3, 20 g *Elaeagnus angustifolia*, 50 g water and 30 g honey are adopted in the present embodiment, and peel scales of the *Elaeagnus angustifolia* are rubbed with water in the present step;

S2. uniformly mixing the fresh milk, the white sugar as well as the *Elaeagnus angustifolia* powder, the apple pear juice and the *Elaeagnus angustifolia* honey drink obtained in the step S1 according to a ratio, maintaining a temperature at 60° C.-70° C. for 60 minutes, and uniformly stirring for 30 minutes;

S3. homogenizing the mixture obtained in the step S2 through a homogenizer, and then enabling the mixture to enter a sterilization machine for sterilizing at 96.6° C.;

S4. cooling to 40° C.-44° C., adding the yoghurt starter, uniformly stirring, adding sterilized wild Chinese wolfberry grains, filling, and fermenting at 40° C.-43° C. for 4-8 hours after filling completion; and S5. rapidly cooling to 4° C.-15° C. after fermenting, and performing after ripening.

Those skilled in the art may make various corresponding modifications and variations according to the above technical solutions and concepts, while all the modifications and variations should be included in the protection scope of claims of the present invention.

What is claimed is:

1. An *Elaeagnus angustifolia* yoghourt, comprising the following raw materials in percentage by weight;
   a) fresh milk—86%-90%;
   b) yoghurt starter—2%-4%;
   c) white sugar—2%-6%;
   d) *Elaeagnus angustifolia* powder—1%-3%;
   e) apple-pear juice—1%-2%; and
   f) *Elaeagnus angustifolia* honey drink—1%-2%.

2. A manufacturing method of the *Elaeagnus angustifolia* yoghourt according to claim 1, comprising the following steps:
   S1. (a) selecting clean *Elaeagnus angustifolia* which is steamed, baked and milled to obtain an *Elaeagnus angustifolia* powder for later use,
   (b) cleaning apples and pears and making a juice from them, and filtering the juice through a filter cloth with a mesh size of over 200 to obtain an apple-pear juice;
   (c) preparing an *Elaeagnus angustifolia* honey drink by:
   (i) selecting an amount of clean *Elaeagnus angustifolia*,
   (ii) adding the *Elaeagnus angustifolia* and water into a pot and boiling for 30 minutes,
   (iii) then adding honey, wherein the weight ratio of the *Elaeagnus angustifolia* to the water to the honey is 2:5:3,
   (iv) taking the product obtained in step (iii) out of the pot and cooling it;
   S2. uniformly mixing the fresh milk, the white sugar, the *Elaeagnus angustifolia* powder, the apple-pear juice and the *Elaeagnus angustifolia* and honey mixture obtained in step S1 according to the weight percentage in claim 1, maintaining a temperature at 60-70° C. for 60 minutes, and uniformly stirring for 30 minutes to obtain a mixture;
   S3. homogenizing the mixture obtained in the step S2 through a homogenizer, and then sterilizing the homogenized mixture at 96.6° C.;
   S4. then cooling the sterilized mixture to 40-44° C., adding a yoghurt starter culture, uniformly stirring, adding sterilized wild Chinese wolfberry grains, filling the composition obtained after adding the wild Chinese wolfberry grains into another container, and fermenting the contents of this container at 40-43° C. for 4-8 hours; and
   S5. cooling the fermented composition to 4-15° C.

* * * * *